(12) United States Patent
Tanaka et al.

(10) Patent No.: US 12,038,334 B2
(45) Date of Patent: Jul. 16, 2024

(54) INTERNAL TEMPERATURE MEASUREMENT DEVICE AND METHOD

(71) Applicant: Nippon Telegraph and Telephone Corporation, Tokyo (JP)

(72) Inventors: Yujiro Tanaka, Tokyo (JP); Daichi Matsunaga, Tokyo (JP); Michiko Seyama, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 352 days.

(21) Appl. No.: 17/598,951

(22) PCT Filed: Apr. 9, 2020

(86) PCT No.: PCT/JP2020/015942
§ 371 (c)(1),
(2) Date: Sep. 28, 2021

(87) PCT Pub. No.: WO2020/218006
PCT Pub. Date: Oct. 29, 2020

(65) Prior Publication Data
US 2022/0187143 A1    Jun. 16, 2022

(30) Foreign Application Priority Data
Apr. 24, 2019   (JP) ................................. 2019-082673

(51) Int. Cl.
*G01K 11/24*   (2006.01)
*A61B 5/01*    (2006.01)

(52) U.S. Cl.
CPC ............... *G01K 11/24* (2013.01); *A61B 5/01* (2013.01)

(58) Field of Classification Search
CPC ................................. G01K 11/24; A61B 5/01
See application file for complete search history.

(56) References Cited

U.S. PATENT DOCUMENTS

| 2002/0134159 A1* | 9/2002 | He | G01N 29/46 |
| | | | 73/579 |
| 2004/0030227 A1* | 2/2004 | Littrup | A61N 7/02 |
| | | | 600/300 |

(Continued)

FOREIGN PATENT DOCUMENTS

| JP | S61154666 A | 7/1986 |
| JP | 2008070340 A | 3/2008 |

(Continued)

OTHER PUBLICATIONS

Huang et al., "A Wearable Thermometry for Core Body Temperature Measurement and Its Experimental Verification," IEEE Journal of Biomedical and Health Informatics, vol. 21, No. 3, May 2017, pp. 708-714.

(Continued)

*Primary Examiner* — Jason M Ip
(74) *Attorney, Agent, or Firm* — SLATER MATSIL, LLP

(57) ABSTRACT

An internal temperature measurement device includes a sound wave sensor that transmits a sound wave to a subject and receives a reflected sound wave reflected by the subject, a time measurement device that measures an elapsed time elapsed between transmission of the sound wave from the sound wave sensor and reception of the reflected sound wave, a sound velocity calculator that calculates a sound velocity in the subject according to the elapsed time measured by the time measurement device, and an internal temperature derivation device that determines an internal temperature of the subject according to the sound velocity calculated by the sound velocity calculator.

6 Claims, 5 Drawing Sheets

(56) References Cited

U.S. PATENT DOCUMENTS

2009/0030312 A1\* 1/2009 Hadjicostis .......... A61B 8/4488
                                                                 606/33
2019/0262074 A1\* 8/2019 Kusumoto ........... A61B 5/0035

FOREIGN PATENT DOCUMENTS

| JP | 2010181174 A | 8/2010 |
| JP | 2011002326 A | 1/2011 |
| JP | 2017203745 A | 11/2017 |
| WO | 2010106633 A1 | 9/2010 |

OTHER PUBLICATIONS

Nakagawa et al., "Proposal of Wearable Deep Thermometer with MEMS Heat Flux Sensor," IEEJ Journal E (Sensors and Micromachines), IEEJ Transactions on Sensors and Micromachines, Vo 1.135 No. 8, The Institute of Electrical Engineers of Japan., Feb. 2015, pp. 343-348.

\* cited by examiner

INTERNAL TEMPERATURE MEASUREMENT DEVICE AND METHOD

CROSS-REFERENCE TO RELATED APPLICATIONS

This application is a national phase entry of PCT Application No. PCT/JP2020/015942, filed on Apr. 9, 2020, which claims priority to Japanese Application No. 2019-082673, filed on Apr. 24, 2019, which applications are hereby incorporated herein by reference.

TECHNICAL FIELD

The present invention relates to an internal temperature measurement device and a method configured to measure an internal temperature of a subject such as a living body.

BACKGROUND

As a thermometer that measures a core body temperature of a subject, a heating type thermometer that uses a heating element (heater) is known. Nevertheless, a heating type thermometer has a problem in that the thermometer consumes a large amount of power, making it difficult to perform continuous measurement over a long period of time.

On the other hand, as another type of thermometer that measures a core body temperature of a subject, a non-heating type thermometer having two sets of heat flow detection structures is known (refer to Non Patent Literature 1 and 2). The two sets of heat flow detection structures have a structure in which a first temperature sensor and a second temperature sensor are separated by a heat-insulating material. In a non-heating type thermometer, as long as a thermal resistance of the heat-insulating material and a thermal resistance of the subject are known, the core body temperature of the subject can be calculated from the measured values of the first and second temperature sensors.

Nevertheless, because a tissue of the subject and a shape of the tissue differ with location or physiological sweat and changes in blood flow, the thermal resistance in the subject interior also differs with location. Such a difference in thermal resistance in the subject interior is an uncertainty during core body temperature measurement, and there is a problem in that the difference causes deterioration in accuracy during core body temperature calculation.

CITATION LIST

Non Patent Literature

Non Patent Literature 1: Shinya Nakagawa, Masao Shimizu, Tsuyoshi Hamaguchi, "Wearable Core Temperature Thermometer Implemented by the MEMS Heat Flux Sensor," IEEJ Transactions on Sensors and Micromachines, Vol. 135, No. 8, 343, 348, 2015.

Non Patent Literature 2: Ming Huang, et al., "A Wearable Thermometry for Core Body Temperature Measurement and its Experimental Classification," IEEE Journal of Biomedical and Health Informatics, Vol. 21, No. 3, 708-714, 2017.

SUMMARY

Technical Problem

In order to solve the problem described above, an object of embodiments of the present invention is to provide an internal temperature measurement device and a method capable of improving an accuracy of measurement of an internal temperature of a subject.

Means for Solving the Problem

An internal temperature measurement device according to an aspect of embodiments of the present invention includes a sound wave sensor configured to transmit a sound wave to a subject and receive a reflected sound wave reflected by the subject, a time measurement unit configured to measure an elapsed time elapsed between transmission of the sound wave from the sound wave sensor and reception of the reflected sound wave, a sound velocity calculation unit configured to calculate a sound velocity in the subject on the basis of the elapsed time measured by the time measurement unit, and an internal temperature derivation unit configured to determine an internal temperature of the subject on the basis of the sound velocity calculated by the sound velocity calculation unit.

Further, the internal temperature measurement device according to the aspect of embodiments of the present invention may further include a storage unit configured to store a relationship between the sound velocity in the subject and the internal temperature of the subject in advance. The internal temperature derivation unit may refer to the storage unit to determine the internal temperature of the subject corresponding to the sound velocity calculated by the sound velocity calculation unit.

Further, the internal temperature measurement device according to the aspect of embodiments of the present invention may further include a time calculation unit configured to calculate a penetration time required for the sound wave to pass through the subject. The sound wave sensor may transmit the sound wave to a target area of internal temperature measurement, the target area being an area where a plurality of known structures exist in an interior of the subject, the time measurement unit may measure, for each of a plurality of the reflected sound waves, the elapsed time elapsed between transmission of the sound wave from the sound wave sensor to reception of the reflected sound wave, the time calculation unit may calculate the penetration time required for the sound wave to pass through a route between the plurality of known structures in the subject on the basis of a measurement result of the time measurement unit, and the sound velocity calculation unit may calculate the sound velocity in the route between the plurality of known structures from the penetration time calculated by the time calculation unit and a known distance between the plurality of known structures.

Further, the internal temperature measurement device according to the aspect of embodiments of the present invention may further include an acoustic matching layer provided between the sound wave sensor and the subject.

Further, an internal temperature measurement method according to another aspect of embodiments of the present invention includes transmitting a sound wave to a subject and receiving a reflected sound wave reflected by the subject, measuring an elapsed time elapsed between transmission of the sound wave and reception of the reflected sound wave, calculating a sound velocity in the subject on the basis of the elapsed time measured in the measuring of the elapsed time, and determining an internal temperature of the subject on the basis of the sound velocity calculated in the calculating of the sound velocity.

Effects of Embodiments of the Invention

According to embodiments of the present invention, a time elapsed between transmission of a sound wave from a sound wave sensor to a subject and reception of a reflected sound wave is measured, a sound velocity in the subject is calculated on the basis of this time, and an internal temperature of the subject is determined on the basis of this sound velocity, thereby making it possible to estimate the internal temperature of the subject without relying on a difference in thermal resistance in the subject interior and improve an accuracy of measurement of the internal temperature of the subject.

DETAILED DESCRIPTION OF ILLUSTRATIVE EMBODIMENTS

Principles of Embodiments of the Invention

When a sound wave is transmitted into a subject from a subject surface, the sound wave is reflected a plurality of times by a plurality of structures, such as bones, for example, in the subject along various routes and returns at various times. The time required to pass through a specific reflection route can be determined by appropriately computing this time. It is possible to estimate a sound velocity in the subject by taking the specific reflection route for a known distance, such as between a bone and a bone. The sound velocity in the subject and a temperature in the subject have, for example, a relationship such as that illustrated in FIG. 1. Accordingly, the temperature in the subject in the specific reflection route can be estimated from the relationship illustrated in FIG. 1. When the subject is a living body, the relationship between the sound velocity in the living body and a core temperature of the living body, although different according to area, is, for example, as illustrated in FIG. 2.

EMBODIMENTS

Figure 3:
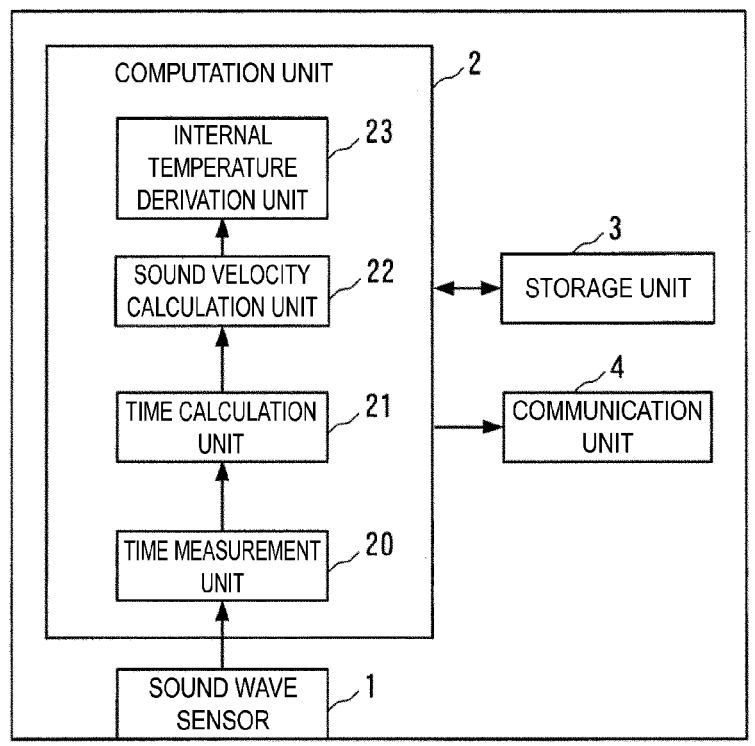
FIG. 3 is a block diagram illustrating a configuration of an internal temperature measurement device according to an embodiment of the present invention.

Embodiments of the present invention will be described below with reference to the drawings. FIG. 3 is a block diagram illustrating a configuration of an internal temperature measurement device according to an embodiment of the present invention. The internal temperature measurement device includes a sound wave sensor 1 that transmits a sound wave to a subject and receives a reflected sound wave reflected by the subject, a computation unit 2 that determines an internal temperature of the subject, a storage unit 3 that accumulates various data required to measure the internal temperature and measurement results of the internal temperature, and a communication unit 4 for communicating with an external device. The computation unit 2 includes a time measurement unit 20, a time calculation unit 21, a sound velocity calculation unit 22, and an internal temperature derivation unit 23.

Figure 4:
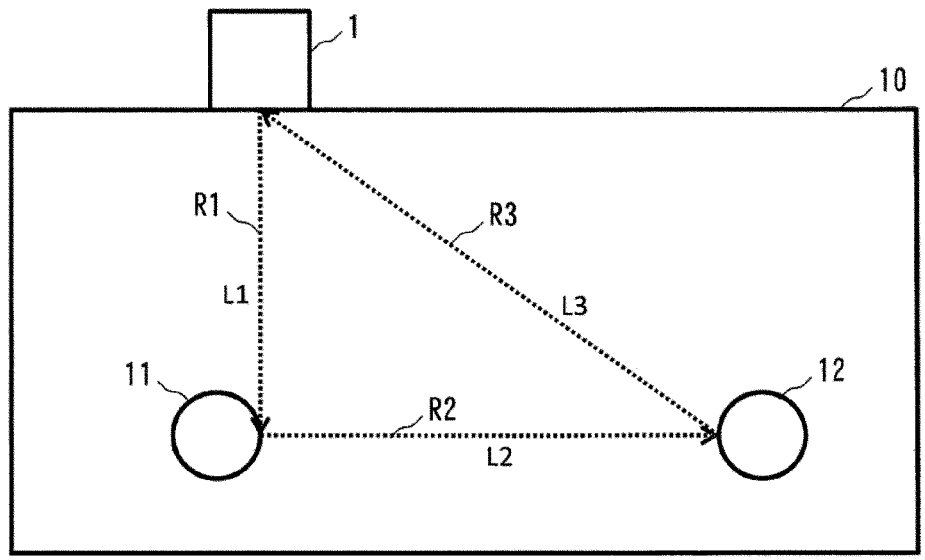
FIG. 4 is a diagram explaining an internal temperature measurement method according to an embodiment of the present invention.

In this embodiment, a location in the subject with at least two structures, such as at least two bones in the case of a living body, for example, is selected as a target area for internal temperature measurement. An internal temperature measurement method according to embodiments of the present invention will now be described with reference to the simplest example in which two bones are aligned as structures 11, 12 in a subject 10 (living body), as illustrated in FIG. 4.

When a sound wave is transmitted from the sound wave sensor 1 disposed on a surface of the subject 10 toward the subject 10, there are three ways in which the sound wave returns to the sound wave sensor 1.

(I) The sound wave passes through a route $R_1$, is reflected by the structure 11, and returns to the sound wave sensor 1 following the route $R_1$ in reverse.

(II) The sound wave passes through a route $R_3$, is reflected by the structure 12, and returns to the sound wave sensor 1 following the route $R_3$ in reverse.

(III) The sound wave passes through the route $R_1$, is reflected by the structure 11, subsequently passes through a route $R_2$, is reflected by the structure 12, and returns to the sound wave sensor 1 through the route $R_3$.

Figure 5:
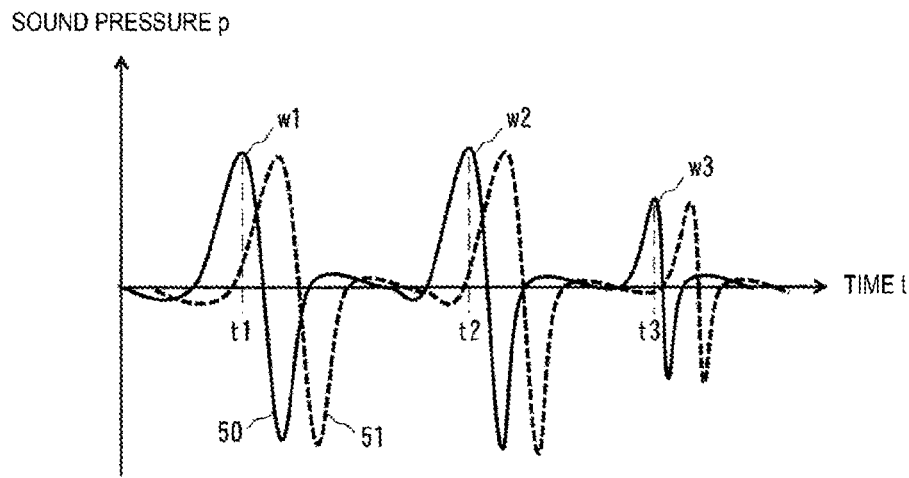
FIG. 5 is a diagram illustrating one example of a waveform of a reflected sound wave observed by a sound wave sensor in an embodiment of the present invention.

Given $w_1$, $w_2$, $w_3$ as the reflected sound waves returning to the sound wave sensor 1 in the cases of (I), (II), (III) described above, respectively, the reflected sound waves $w_1$, $w_2$, $w_3$ are observed at the sound wave sensor 1 after times $t_1$, $t_2$, $t_3$ following transmission of the sound wave from the sound wave sensor 1 (FIG. 5). Note that a solid line 50 in FIG. 5 indicates, for example, a first measurement result, and a dashed line 51 indicates, for example, a second measurement result.

Given $L_1$ as a distance of the route $R_1$ between the sound wave sensor 1 and the structure 11, $L_2$ as a distance of the route $R_2$ between the structure 11 and the structure 12, $L_3$ as a distance of the route $R_3$ between the sound wave sensor 1 and the structure 12, and V as the sound velocity, the times $t_1$, $t_2$, $t_3$ are expressed by the following equations:

$$t_1 = 2 \times L_1/V \ldots \quad (1)$$

$$t_2 = 2 \times L_3/V \ldots \quad (2)$$

$$t_3 = (L_1 + L_2 + L_3)/V \ldots \quad (3)$$

However, the sound velocity V varies depending on temperature, and thus, in the route $R_1$ and the route $R_3$, is affected by the temperature of the subject 10, particularly the temperature of a surface layer which has a large effect. Further, when the subject 10 is a living body, the distances $L_1$, $L_3$ are likely to change due to a flexibility of the living body.

On the other hand, as long as the route $R_2$ between the structure 11 and the structure 12 is in a location sufficiently deep from the surface layer of the subject 10, the sound velocity V is not affected by the surface layer of the subject 10. Thus, the sound velocity in the route $R_2$ is selectively determined from the times $t_1$, $t_2$, $t_3$.

Here, a time tr required for the sound wave to pass through the route $R_2$ can be determined as follows, requiring only subtraction of half the time required for the sound wave to pass back and forth through the routes $L_1$, $L_3$ ($t_1/2$, $t_2/2$) from the time $t_3$ required for the sound wave to pass through the routes $L_1$, $L_2$, $L_3$:

$$tr = t_3 - (t_1 + t_2)/2 \ldots \quad (4)$$

From the time tr required for the sound wave to pass through the route $R_2$, a sound velocity $V_2$ in the route $R_2$ is obtained by the following equation:

$$V_2 = L_2/tr \ldots \quad (5)$$

Figure 1:
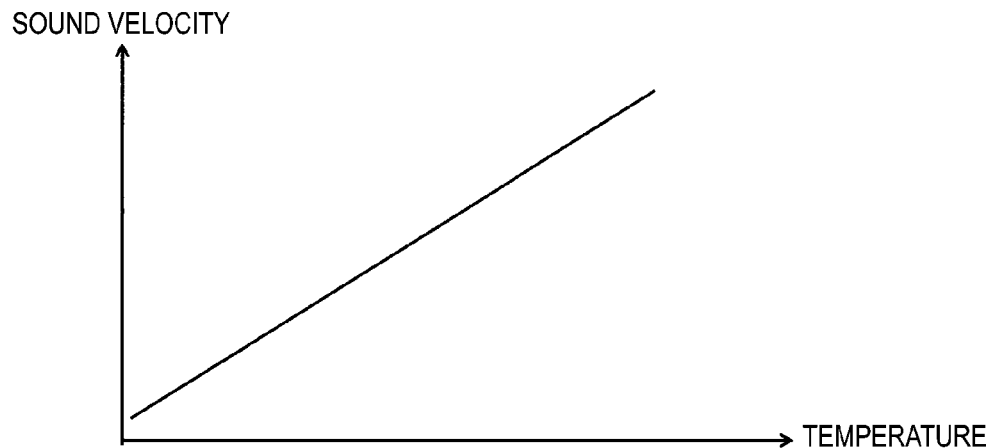
FIG. 1 is a diagram illustrating an example of a relationship between a sound velocity in a subject and a temperature in the subject.
Figure 2:
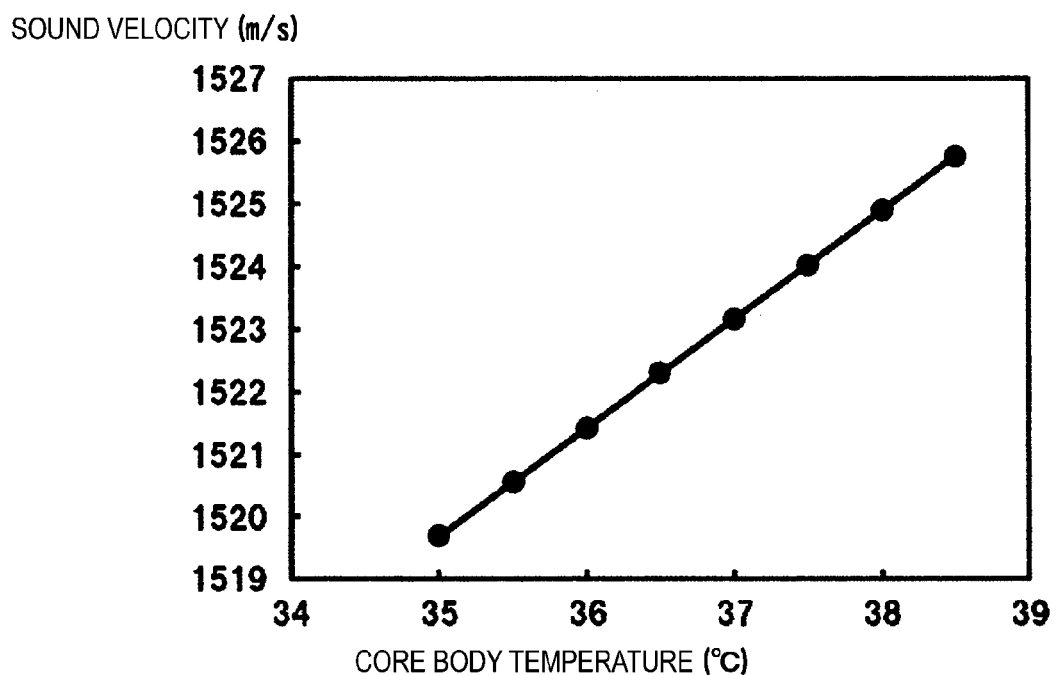
FIG. 2 is a diagram illustrating an example of a relationship between a sound velocity in a living body and a core temperature of the living body.

As illustrated in FIGS. 1 and 2, by examining the relationship between the sound velocity in the subject 10 and the internal temperature of the subject 10, it is possible to determine the internal temperature (core temperature) of the subject 10 corresponding to the sound velocity $V_2$.

When the relationship between the sound velocity in the subject 10 and the internal temperature of the subject 10 is examined, in a case where the subject 10 is a complex subject such as a living body, for example, the temperature (for example, rectal temperature, esophageal temperature, and eardrum temperature) near the target area of internal temperature measurement is obtained using a probe of a thermometer or the like, and the sound velocity near the target area is obtained using an ultrasound probe or the like. The relationship between the sound velocity and the temperature obtained from this result may be defined as the relationship between the sound velocity in the subject 10 and the internal temperature of the subject 10.

Further, the relationship between the sound velocity in the subject 10 and the internal temperature of the subject 10 may be examined by an experiment using a material having a similar structure and physical properties as those of the subject 10 or examined ex-vivo using a cultured tissue similar to that of the subject 10.

Figure 6:
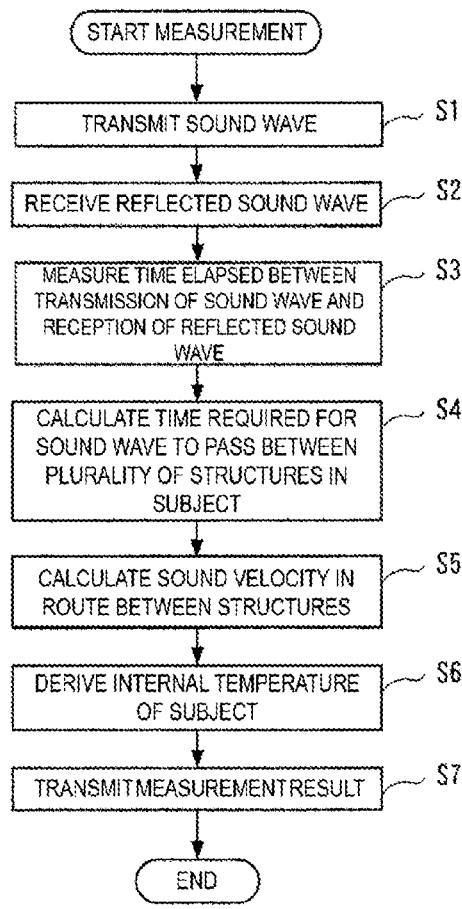
FIG. 6 is a flowchart explaining an operation of the internal temperature measurement device according to an embodiment of the present invention.

FIG. 6 is a flowchart explaining an operation of the internal temperature measurement device according to this embodiment. The sound wave sensor 1 transmits a sound wave toward the subject 10 (FIG. 6, step $S_1$) and receives the reflected sound wave returning from the subject 10 (FIG. 6, step $S_2$).

The time measurement unit 20 in the computation unit 2 measures, for each of a plurality of the reflected sound waves, the times ($t_1$, $t_2$, $t_3$ described above) elapsed between transmission of the sound wave from the sound wave sensor 1 and reception of the reflected sound wave (FIG. 6, step $S_3$). Note that it is only required that the elapsed time be a time between transmission of the sound wave and acquisition of a peak of the reflected sound wave.

The time calculation unit 21 in the computation unit 2 calculates, on the basis of the measurement result of the time measurement unit 20, the time tr required for the sound wave to pass through the route $R_2$ between the plurality of known structures 11, 12 in the subject 10 in a transmission direction of the sound wave by equation (4) (FIG. 6, step $S_4$).

The sound velocity calculation unit 22 in the computation unit 2 calculates the sound velocity $V_2$ in the route $R_2$ between the structures 11, 12 from the time tr calculated by the time calculation unit 21 and the known distance $L_2$ between the structures 11, 12, by equation (5) (FIG. 6, step $S_5$).

The internal temperature derivation unit 23 in the computation unit 2 refers to the storage unit 3 in which the relationship between the sound velocity V in the subject 10 and an internal temperature Tref of the subject 10 is stored in advance, and determines the internal temperature Tref of the subject 10 corresponding to the sound velocity V calculated by the sound velocity calculation unit 22 (FIG. 6, step $S_6$).

The communication unit 4 transmits information related to the internal temperature Tref of the subject 10 obtained by the internal temperature derivation unit 23 to an external device (for example, a server that collects measured values of the internal temperature) (FIG. 6, step $S_7$).

Figure 7:
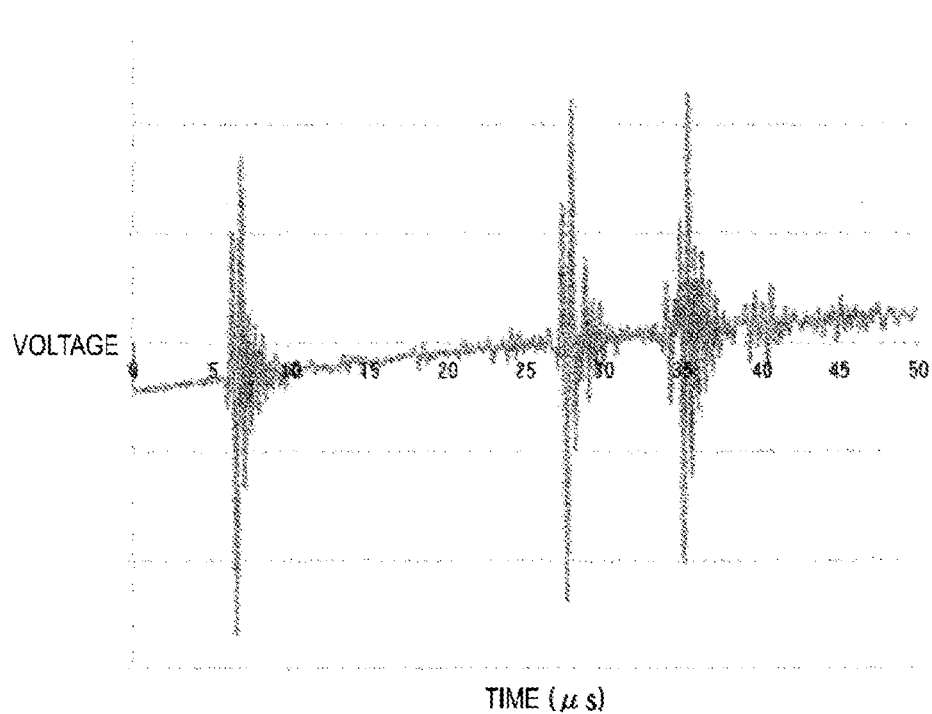
FIG. 7 is a diagram illustrating an example of a waveform of a reflected sound wave observed in a measurement experiment of internal temperature.
Figure 8:
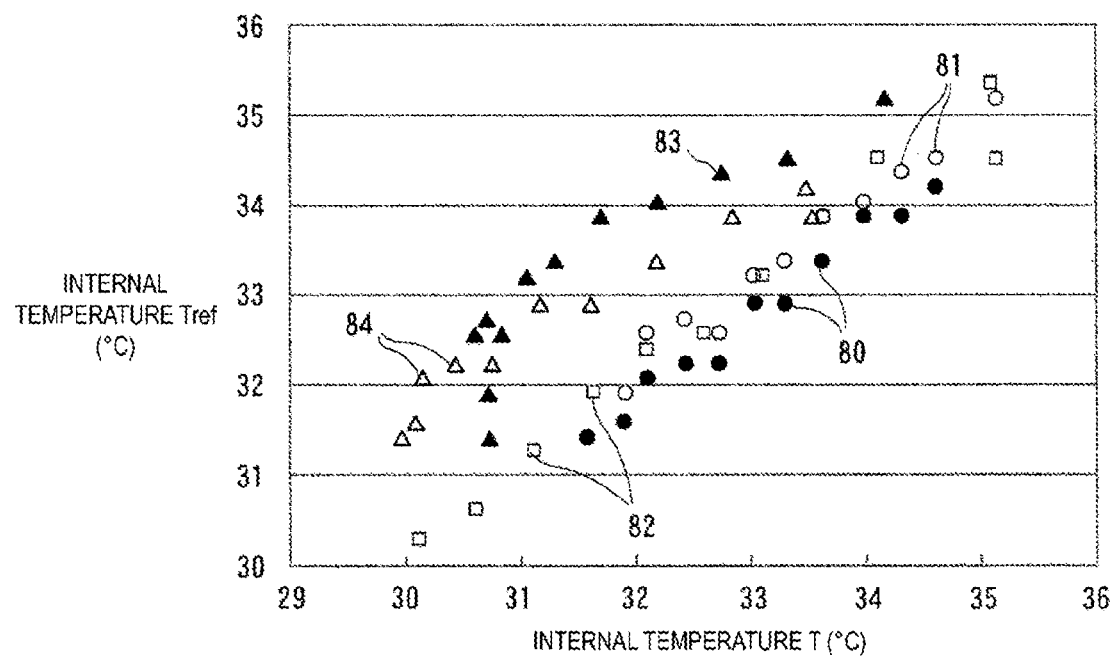
FIG. 8 is a diagram explaining an effect of the internal temperature measurement device according to an embodiment of the present invention.

FIG. 7 is a diagram illustrating one example of a waveform of a reflected sound wave observed in a measurement experiment of internal temperature. FIG. 8 is a diagram explaining an effect of this embodiment. T of the horizontal axis in FIG. 8 indicates, for example, the internal temperature of the subject 10 determined by inserting a probe of a thermometer into the subject 10, and Tref of the vertical axis indicates the internal temperature of the subject 10 determined by the internal temperature measurement device of this embodiment.

The number 80 in FIG. 8 indicates the measurement result when the surface temperature and the internal temperature of the subject 10 are the same (for example, when the living body is resting), and the number 81 indicates the measurement result when the internal temperature is measured while the surface temperature of the subject 10 is changing. The number 82 indicates the measurement result when the internal temperature is measured in a state where there is a flow in the surface layer of the subject 10 (for example, a state in which blood flow in the living body is markedly changing due to exercise or the like).

Further, the number 83 in FIG. 8 indicates the result of measuring the surface temperature of the subject 10 while the surface temperature and internal temperature of the subject 10 are in the same state (for example, when the living body is resting), and the number 84 indicates the result of measuring the surface temperature of the subject 10 while the surface temperature of the subject 10 is changing.

According to FIG. 8, it is understood that the internal temperature T of the of the subject 10 measured with a thermometer is in good agreement with the internal temperature Tref of the subject 10 determined by the internal temperature measurement device of this embodiment.

Further, it is understood that when the surface temperature of the subject 10 is measured using the internal temperature measurement device of this embodiment, there is a difference from the surface temperature of the subject 10 measured by the thermometer.

Figure 9:
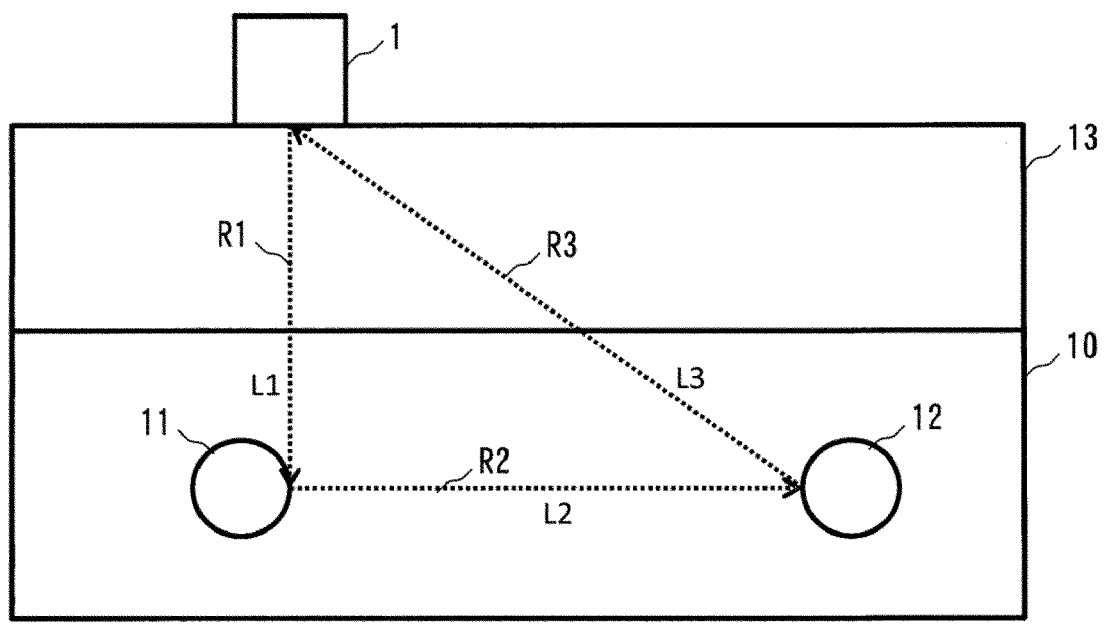
FIG. 9 is a diagram illustrating an example in which an acoustic matching layer is provided between the sound wave sensor and the subject in an embodiment of the present invention.

In this embodiment, when the area of the subject 10 to be measured is close to the sound wave sensor 1 and a sufficient wavenumber is not applied, an acoustic matching layer 13 may be provided between the sound wave sensor 1 and the subject 10 as illustrated in FIG. 9. At this time, the acoustic impedance of the acoustic matching layer 13 is preferably close to that of the subject 10. Specifically, when the subject 10 is a living body, the acoustic impedance may be adjusted to approximately 1.5 MRayl using silicone rubber, resin, or the like as the acoustic matching layer 13.

Figure 10:
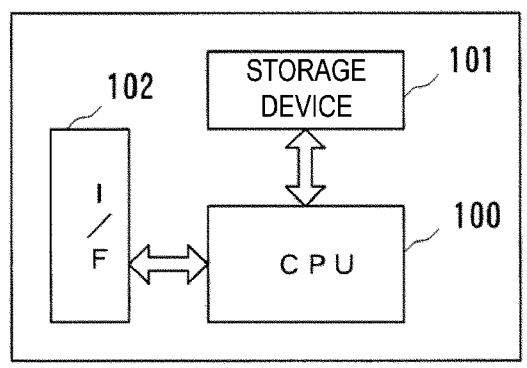
FIG. 10 is a block diagram illustrating a configuration example of a computer that realizes the internal temperature measurement device according to an embodiment of the present invention.

The computation unit 2 and the storage unit 3 of the internal temperature measurement device described in this embodiment can be realized by a computer including a central processing unit (CPU), a storage device, and an interface, and programs for controlling these hardware resources. A configuration example of this computer is illustrated in FIG. 10. The computer includes a CPU 100, a storage device 101, and an interface device (hereinafter abbreviated as I/F) 102. The sound wave sensor 1, the communication unit 4, and the like are connected to the I/F 102. In such a computer, a program for realizing the internal temperature measurement method of embodiments of the present invention is stored in the storage device 101. The CPU 100 executes the processes described in this embodiment in accordance with the program stored in the storage device 101.

INDUSTRIAL APPLICABILITY

Embodiments of the present invention can be applied to techniques for measuring the internal temperature of a subject, such as a living body.

REFERENCE SIGNS LIST

1 Sound wave sensor
2 Computation unit
3 Storage unit
4 Communication unit
10 Subject
11, 12 Structure
13 Acoustic matching layer
20 Time measurement unit
21 Time calculation unit
22 Sound velocity calculation unit
23 Internal temperature derivation unit.

The invention claimed is:

1. An internal temperature measurement device comprising:
   a sound wave sensor configured to:
      transmit a sound wave to a subject comprising at least two internal structures having a known distance between them; and
      receive a plurality of sound wave reflections in response to the sound wave, wherein:
         a first sound wave reflection of the plurality of sound wave reflections is reflected from a first internal structure of the at least two internal structures back to the sound wave sensor in a first time and along a first route,
         a second sound wave reflection of the plurality of sound wave reflections is reflected from a second internal structure of the at least two internal structures back to the sound wave sensor in a second time and along a second route different from the first route, and
         a third sound wave reflection of the plurality of sound wave reflections is reflected from the first internal structure to the second internal structure, and then from the second internal structure back to the sound wave sensor in a third time and along a third route that spans the known distance and is different from the first route and the second route;
   a time measurement device configured to measure the first time, the second time, and the third time;
   a sound velocity calculator configured to calculate a sound velocity between the at least two internal structures based on the known distance between the at least two internal structures, the first time, the second time, and the third time; and
   an internal temperature derivation device configured to determine an internal temperature between the at least two internal structures of the subject according to the sound velocity calculated by the sound velocity calculator.

2. The internal temperature measurement device according to claim 1, further comprising:
   a storage device configured to store a relationship between the sound velocity between the at least two internal structures in the subject and the internal temperature of the subject in advance, wherein, the internal temperature derivation device refers to the storage device to determine the internal temperature of the subject corresponding to the sound velocity calculated by the sound velocity calculator.

3. The internal temperature measurement device according to claim 1, further comprising:
   an acoustic matching layer between the sound wave sensor and the subject.

4. An internal temperature measurement method comprising:
   transmitting, by a sound wave sensor, a sound wave to a subject comprising at least two internal structures having a known distance between them;
   receiving, by the sound wave sensor, a plurality of sound wave reflections in response to the sound wave, wherein:
      a first sound wave reflection of the plurality of sound wave reflections is reflected from a first internal structure of the at least two internal structures to the sound wave sensor in a first time and along a first route,
      a second sound wave reflection of the plurality of sound wave reflections is reflected from a second internal structure of the at least two internal structures back to the sound wave sensor in a second time and along a second route different from the first route, and
      a third sound wave reflection of the plurality of sound wave reflections is reflected from the first internal structure to the second internal structure, and then from the second internal structure back to the sound wave sensor in a third time and along a third route that spans the known distance and is different from the first route and the second route;
   measuring, by a time measurement device, the first time, the second time, and the third time;
   calculating, by a sound velocity calculator, a sound velocity between the at least two internal structures based on the known distance between the at least two internal structures, the first time, the second time, and the third time; and
   determining an internal temperature between the at least two internal structures of the subject according to the sound velocity.

5. The internal temperature measurement method according to claim 4,
   wherein the determining of the internal temperature includes referring to a storage device that stores, in advance, a relationship between the sound velocity between the at least two internal structures in the subject and the internal temperature of the subject to determine the internal temperature of the subject corresponding to the sound velocity.

6. The internal temperature measurement method according to claim 4 further comprising providing an acoustic matching layer between the sound wave sensor and the subject.

\* \* \* \* \*